United States Patent

Ferko, III

[11] Patent Number: 5,944,016
[45] Date of Patent: Aug. 31, 1999

[54] ADJUSTABLE, COLLAPSIBLE HEAD IMMOBILIZER

[76] Inventor: Joseph G. Ferko, III, 412 Park Creek Rd., Pasadena, Md. 21122

[21] Appl. No.: 09/128,767

[22] Filed: Aug. 4, 1998

Related U.S. Application Data

[60] Provisional application No. 60/064,133, Nov. 3, 1997.

[51] Int. Cl.⁶ .................................................. A61B 19/00
[52] U.S. Cl. .............................. 128/869; 5/637; 128/870
[58] Field of Search .................................. 128/845, 846, 128/869, 870, 876; 5/630, 637, 638

[56] References Cited

U.S. PATENT DOCUMENTS

| | | | |
|---|---|---|---|
| 4,252,113 | 2/1981 | Scire | 5/637 |
| 4,928,711 | 5/1990 | Williams | 128/870 |
| 5,305,754 | 4/1994 | Honeywell | 128/870 |
| 5,360,393 | 11/1994 | Garth | 128/870 |

Primary Examiner—Michael A. Brown
Attorney, Agent, or Firm—Roylance, Abrams, Berdo & Goodman, L.L.P.

[57] ABSTRACT

A head immobilizer for use in emergency situations is formed in a flat, compact shape which is easily formed into an operable configuration. The head immobilizer includes a base and a head stabilizing structure attached to the base. The stabilizing structure includes a pair of inner panels that are hinged to the base at one edge and can be conformed to the shape of the patient's head. An outer support panel is hinged to an opposite end of the inner panel. A slide tab is attached to the outer panel and is coupled for sliding movement with respect to the base. A locking mechanism is provided to lock the sliding tab in position during use. The position of the slide tab with respect to the base adjusts the spacing of the inner panels comfortably to conform to the patient's head.

22 Claims, 4 Drawing Sheets

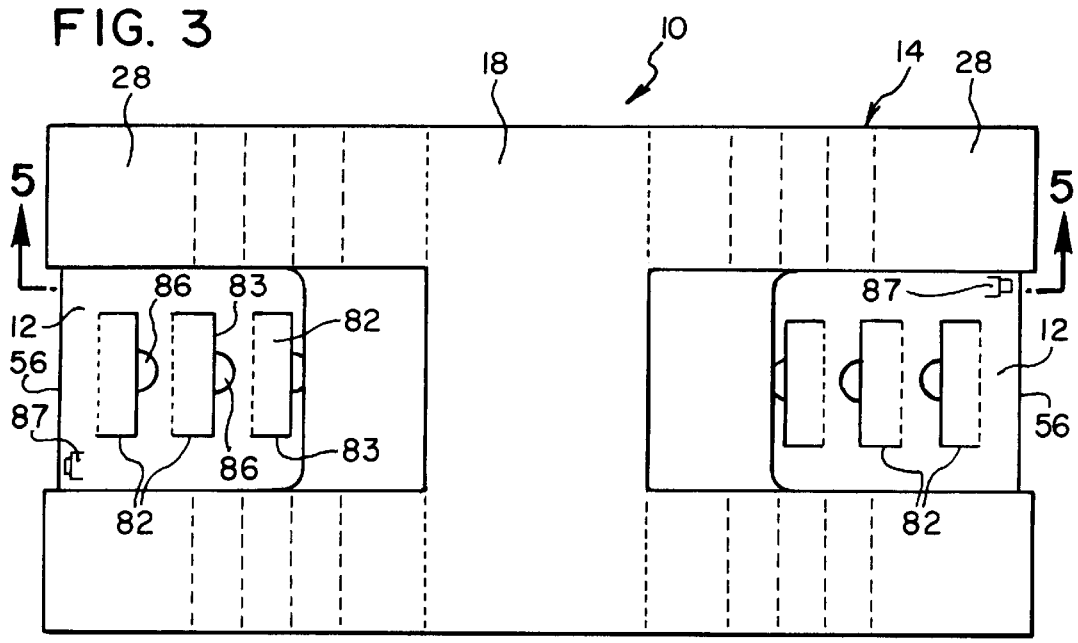
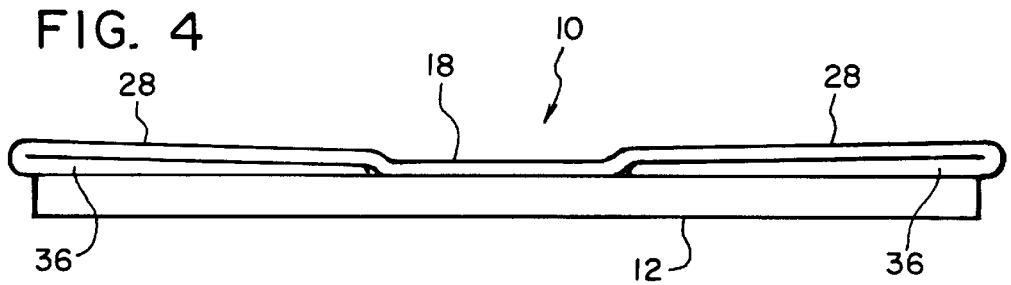
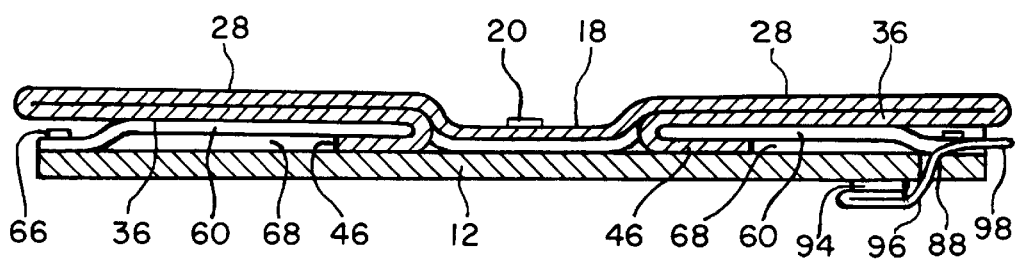

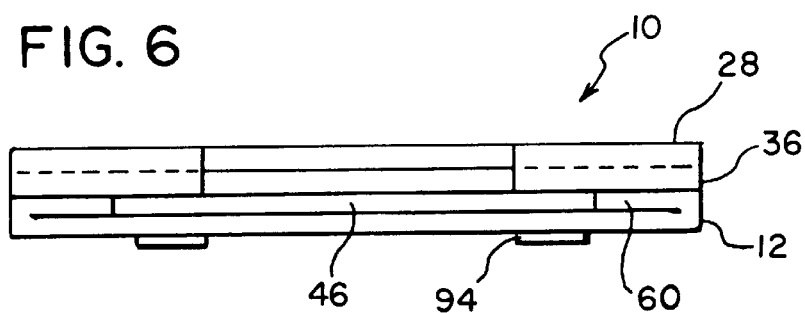
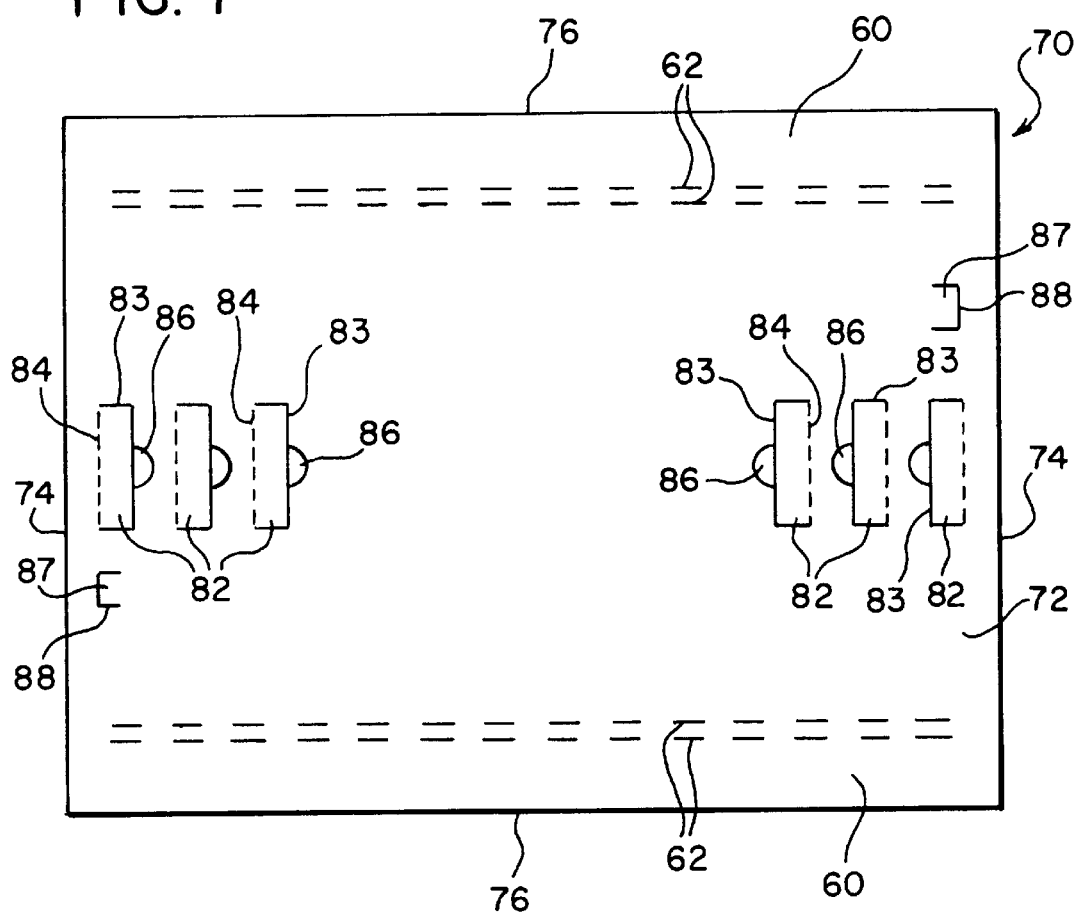

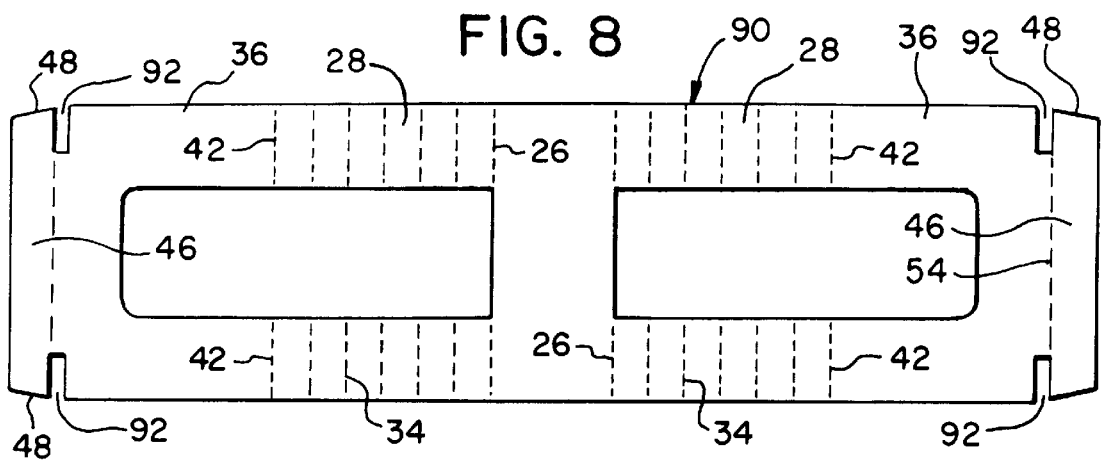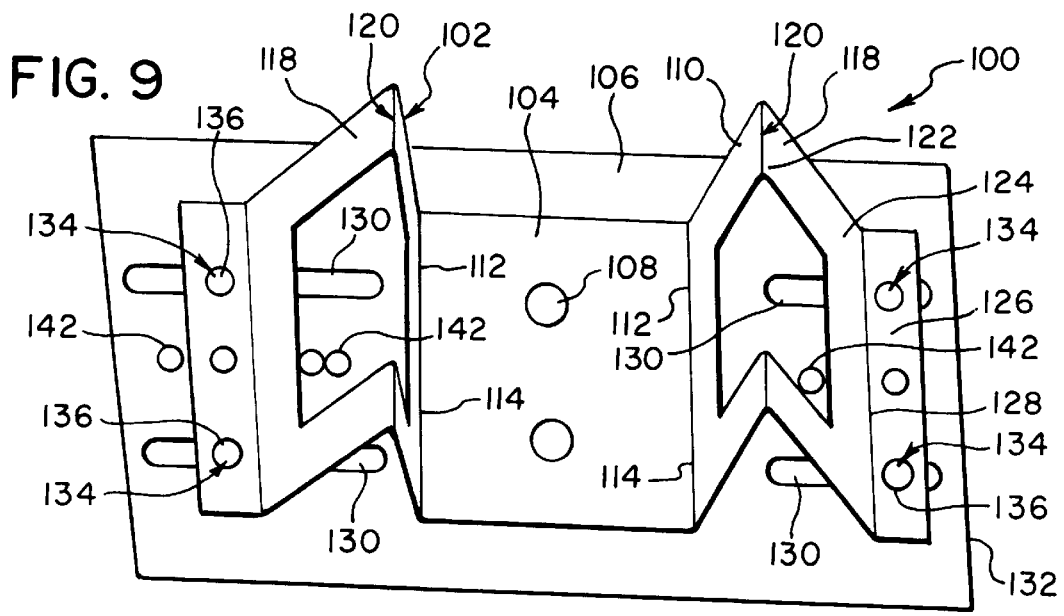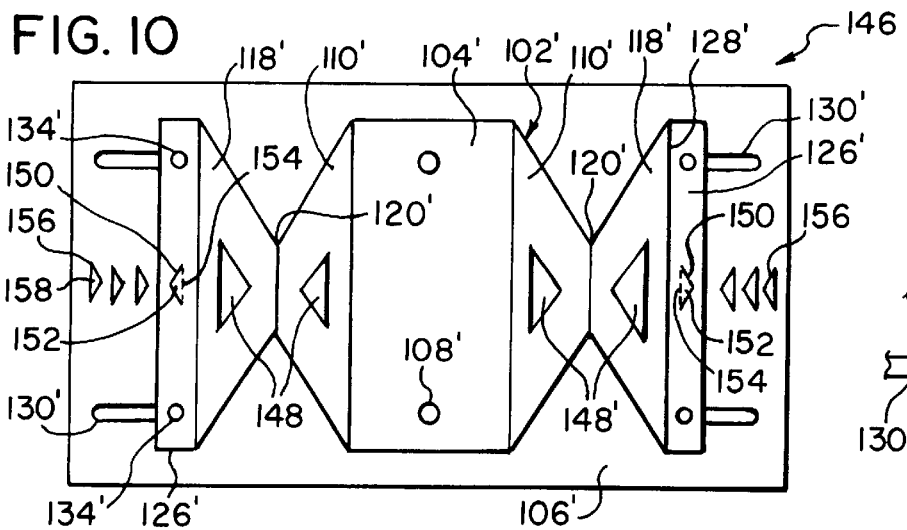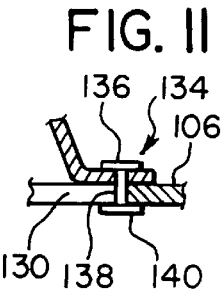

ADJUSTABLE, COLLAPSIBLE HEAD IMMOBILIZER

This application claims the benefit under 35 U.S.C. § 119(e) of U.S. provisional application Ser. No. 60/064,133 filed Nov. 3, 1997.

FIELD OF THE INVENTION

This invention relates to head immobilizers. Specifically, this invention relates to adjustable, collapsible head immobilizers.

BACKGROUND OF THE INVENTION

Head immobilizers are commonly used to stabilize the human head and neck in situations requiring emergency medical attention. These devices are important in safely transporting a patient without aggravating injuries to the cervical spine. In an emergency situation, a patient is evaluated and transported by emergency rescue personnel who have some degree of medical training but who are not medical doctors. The head immobilizers therefore must be readily usable by those without expert knowledge. The majority of head immobilizers to date are either very complex and difficult to use in an emergency, or they are bulky and require valuable storage space in an emergency vehicle. The head immobilizers are currently designed as a flat device for storage and are then folded to form the immobilizers. These prior devices do not include a stable base for supporting the patient's head. These prior devices are typically affixed to a second device such as a rigid support backboard.

U.S. Pat. No. 4,718,412 to Nesbitt discloses one example of a disposable cervical immobilization device. This device is a complex disposable immobilizer requiring a plurality of folds in order to fit the device both over a patient's shoulders and around the patient's torso. This device is complex and difficult to use in an emergency situation where transporting a patient quickly and efficiently is critical to survival.

Another prior cervical immobilization collar is identified as Ambu DisposaBed™ CID & Head Strap. This device is a waterproof, disposable immobilizer made from corrugated material. The device can be folded for storage and is intended to be used in conjunction with a spine board. The device does not include its own stable base. The device uses a second device such as the rigid spine board as a base. This device is attached to a base by means of adhesive tape.

A device identified as Head Vice™ Disposable Head Immobilizer is a cardboard immobilizer device with foam padding on a cardboard base. The device can be attached to a firm backboard using double-sided tape. The device includes side panels which must be extended to fold the device flat for storage. The extended panels have the disadvantage of requiring additional storage space in emergency vehicles.

U.S. Pat. No. 4,928,711 to Williams discloses a head immobilizer and method for immobilizing a patient. The device can be attached to a rigid backboard and includes a base. The device must be bent into place to be secured in a locked position for immobilization of the patient's head. The device can be folded, although it must be extended to fold flat, thereby requiring additional storage space.

The industry lacks an adjustable, collapsible head immobilizer that provides locked support on a fixed base which is compact when folded flat for storage in emergency vehicles. The industry requires a preassembled immobilizer adaptable from infant to adult head sizes.

SUMMARY OF THE INVENTION

The present invention is directed to a head immobilizing device. More particularly, the invention is directed to a head immobilizing device for emergency use which can be removably attached to a spine board.

Accordingly, a primary object of the invention is to provide a head immobilizing device that is collapsible and is able to lay flat during storage and which can be expanded to an operating configuration with minimal effort.

Another object of the invention is to provide a head immobilizing device that is inexpensive and easy to manufacture.

A further object of the invention is to provide a head immobilizing device that is simple to use and which provides proper support to a patient's head during transport.

Another object of the invention is to provide a head immobilizing device that is adjustable to accommodate the size of a patient's head to provide proper support to the head.

The objects of the invention are basically attained by providing a head immobilizer comprising: a base having a longitudinal dimension with longitudinal ends and a transverse dimension with transverse ends; a head immobilizing member attached to the base and including a pair of support members, each of the support members including an inner panel and an outer panel, the inner panel having a first edge hingedly connected to the base and a second edge, the inner panels forming a head immobilizing support structure, the outer panel having a first edge hinged to the second edge of the inner panel, the outer panels defining a support for supporting its respective inner panel in a fixed position with respect to the base; a slide tab hingedly connected to a second edge of each outer panel and being coupled to the base for limited sliding movement along the base, and a locking device for limiting sliding movement of each slide tab with respect to the base.

The objects of the invention are further attained by providing a head immobilizer comprising: a base having a longitudinal dimension with opposite longitudinal edges, and a transverse dimension with opposite transverse the edges; a side panel coupled to the base along each transverse side edge, each side panel being substantially parallel to the base to define a pair of longitudinal slots along the transverse side edges of the base; a pair of head support members attached to the base, each of the support members including an inner head immobilizing support panel and an outer support panel, the inner panel having a first edge hinged to the base and a second end opposite the first end, the outer panel having a first edge hinged to the second edge of the inner panel and a second edge hinged to the base, the inner panels together being capable of cradling a patient's head and the outer panels supporting the inner panels in a head cradling position; each of the outer panels having a slide tab having a first longitudinal edge hinged to the first edge of a respective outer panel, the slide tab having opposite transverse ends received in the longitudinal slots for sliding movement therein, wherein the sliding movement selectively adjusts the space between the inner panels.

The objects, advantages and other salient features of the invention will become apparent to one skilled in the art in view of the drawings and the following detailed description of the invention.

BRIEF DESCRIPTION OF THE DRAWINGS

Referring to the drawings which form a part of this original disclosure in which:

FIG. 3 is a top plan view of the head immobilizing device of FIG. 1 in a folded position for storage;

FIG. 4 is a side elevational view of the folded head immobilizing device of FIG. 3;

FIG. 5 is a side cross-sectional view of the head immobilizing device of FIG. 3 taken along line 5—5;

FIG. 6 is an end view of the head immobilizing device of FIG. 3;

FIG. 7 is a top plan view of the blank of the base for forming the head immobilizing device of FIG. 1;

FIG. 8 is a top plan view of the blank of the support panels for forming the head immobilizing device of FIG. 1;

FIG. 9 is a perspective view of a head immobilizing device in a second embodiment of the invention;

FIG. 10 is a top plan view of a head immobilizing device in a third embodiment of the invention; and FIG. 11 is a partial cross-sectional view of a locking and slide pin of the head immobilizing device of FIGS. 9 and 10.

DETAILED DESCRIPTION OF THE INVENTION

Figure 1:
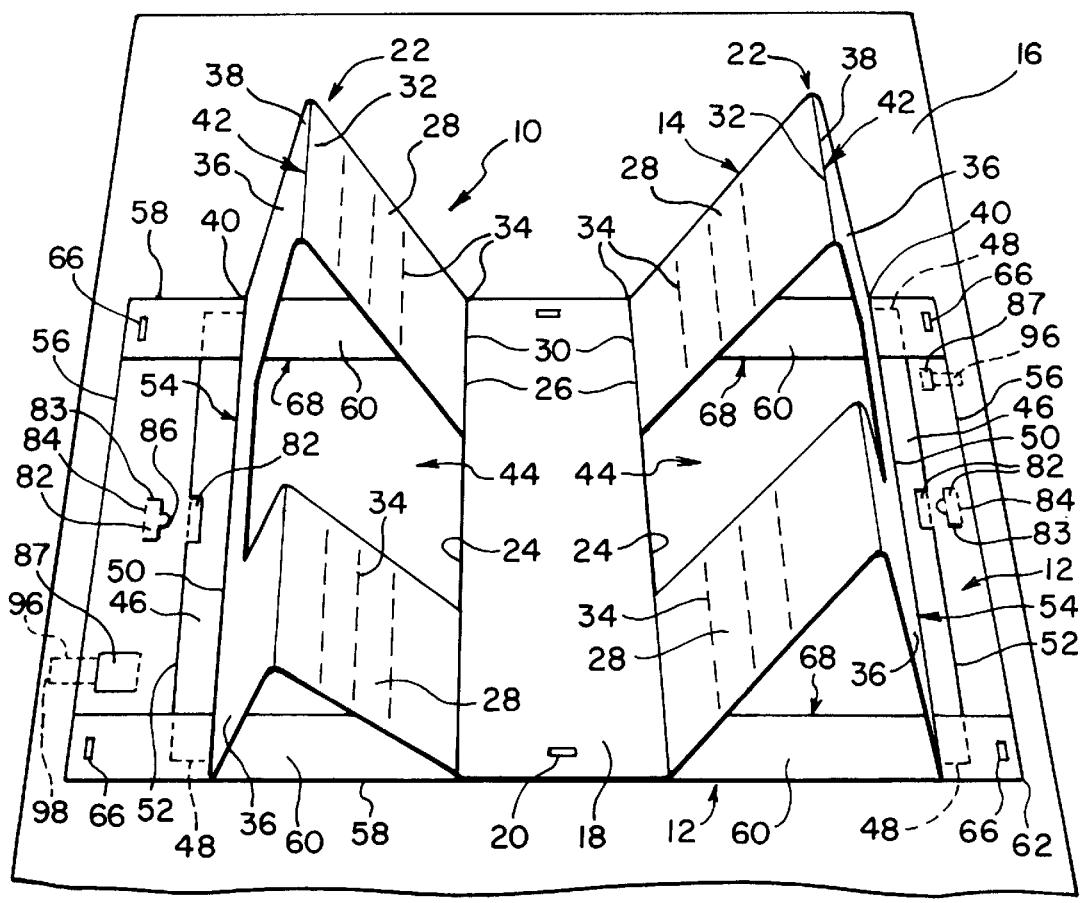
FIG. 1 is a perspective view of the head immobilizing device in a first embodiment of the invention.

The present invention is directed to a head immobilizer that is stored in a flat, compact shape and folded to an upright position to support the head of a patient. The invention is further directed to a head immobilizer device for use in combination with a rigid backboard or spine board.

Referring to the drawings, a preferred embodiment of the invention is illustrated in FIGS. 1–8. As shown in FIGS. 1–5, the head immobilizer 10 includes a base 12 and a head immobilizing support member 14. In the embodiment shown in FIG. 1, the head immobilizer 10 is attached to a rigid spine board 16. The rigid spine board is a standard board used by emergency personnel while transporting a patient to prevent spinal injury.

Referring to FIG. 1, the immobilizer support 14 is made from a single piece of sheet material such as, for example, sheet plastic, cardboard, or other low cost, lightweight material. Preferably, the sheet material is a waterproof or water resistant material. In the embodiment illustrated, immobilizing support member 14 includes a center panel 18 having a substantially rectangular shape. The center panel 18 is attached to the base 12 by a suitable fastener, such as a staple 20 at each end of the panel. A pair of symmetrical support members 22 are coupled to side edges 24 of the center panel 18 along a fold line 26. In the embodiment illustrated, the center panel 18 is a single piece. In further embodiments, the center panel can be two or more members coupled together or independently attached to the base 12.

Figure 2:
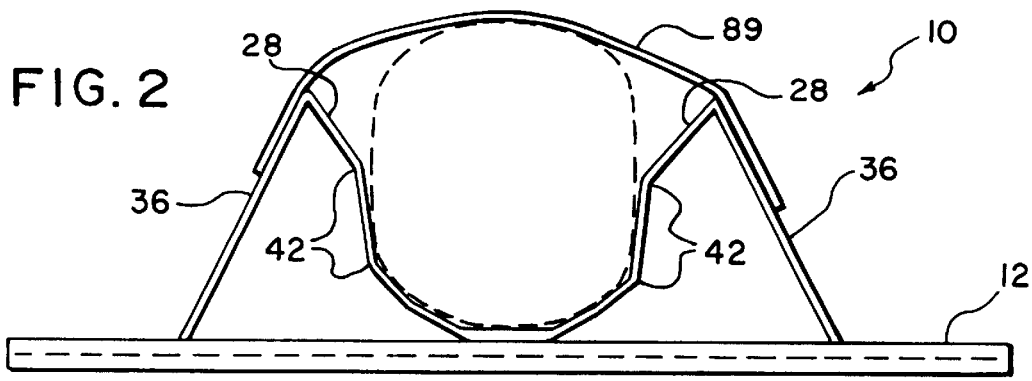
FIG. 2 is a side elevational view of the head immobilizing device of FIG. 1.

Each Support member 22 includes an inner panel 28 which functions as a head supporting panel to cradle the head of a patient. Each inner panel 28 includes a first edge 30 which is coupled to the center panel 18 along the respective fold line 26. A second edge 32 of inner panel 28 is substantially parallel to the first edge 30. A plurality of fold lines 34 extend parallel to the first and second edges 30 and 32, respectively, to enable the inner panel 28 to fold and contour itself about a patient's head as shown in FIG. 2 and as discussed hereinafter in greater detail.

Each support member 22 also includes an outer panel 36 having a first side edge 38 and a second side edge 40. The first side edge 38 of outer panel 36 is coupled to the inner panel 28 along a fold line 42. In the embodiment illustrated, the outer panels 36 are substantially the same length and width as the inner panels 28. In preferred embodiments of the invention, inner panel 28 and outer panel 36 include a cut-out portion 44 to allow access to the ears of a patient. Furthermore, the cut-out portion 44 permits the inner panel 28 to contact the jaw and the top part of the head of the patient to fully support the patient's head while minimizing discomfort.

A slide tab 46 which is coupled to each outer panel 36 has a length substantially equal to the width of the outer panel 36 and the base 12. Slide tabs 46 have distal ends 48, an inner edge 50 and a parallel outer edge 52. The inner edge 50 is coupled to the outer panel 36 along the second side edge 40 by a fold line 54.

The base 12 has a substantially rectangular shape having a longitudinal dimension with longitudinal ends 56 and transverse ends 58 and a flap 60 adjacent to each transverse end 58 by a fold line 62. In preferred embodiments, flaps 60 are coupled to base 12 by a longitudinal fold line. In further embodiments, flaps 60 can be a separate piece attached to base 12 by suitable fasteners or adhesives. As shown in FIG. 1, side panels in the form of flaps 60 have a dimension less than the width of the base 12. The longitudinal ends 64 of each flap 60 are fixed to the base 12 by a suitable fastener, such as, for example, a staple 66. In further embodiments, the ends of each flap 60 can be attached to the base 12 by an adhesive or other mechanical fastener. The flaps 60 form a slot 68 extending in a longitudinal direction with respect to the base 12 along each of the transverse ends 58. The distal ends 48 of the tab 46 are received in the respective slot 68 for sliding in a longitudinal direction with respect to the base 12.

Referring to FIGS. 7 and 8, the head immobilizer 10 is formed from blanks cut from a suitable sheet material, such as cardboard. FIG. 7 shows a blank 70 for forming the base 12. The blank 70 has a substantially rectangular shape defining a center panel 72 having longitudinal ends 74 and transverse ends 76. Fold lines 62 extend parallel to the transverse edges 76 to define the flaps 60 along each transverse end. Flaps 60 are folded along fold lines 60 to overlie the center panel 72 in a substantially parallel position to define the slots 68 in the base 12 as shown in FIG. 1. Blank 70 further includes a plurality of rectangular tabs 82 formed by cut line 83 along three sides such that each tab 82 is connected to the center panel 72 by a fold line 84. A semi-circular cut-out portion 86 provides easy access to the tabs 82 so that they can be folded along the fold line 84 and pivoted upwardly from the base 12. Tabs 87 formed by cut portions 88 are provided for receiving the release liner of a double faced adhesive tape for attaching the immobilizer to spine board 16 as discussed hereinafter in greater detail.

Referring to FIG. 8, a blank 90 is illustrated for forming the head immobilizing support member 14. Blank 90 is cut from a single sheet of cardboard or other sheet material. Blank 90 includes the slide flaps 46 connected by fold lines 54 to the respective outer panel 36. A notched portion 92 is cut from the outer panel 36 adjacent the fold line 54. The inner panels 28 are connected to the center panel 18 and the outer panels 36 by fold lines 34 and 42, respectively.

The head immobilizer 10 is assembled by folding the blank 90 along the fold lines 34, 42 and 54 and inserting the ends 48 of the tabs 46 into the slots 68 of the base 12. As shown in the cross-sectional view of FIG. 5, the slide tabs 46 are received in the slots 68 and the inner panel 28 and outer panel 36 can be folded flat against the base 12. In preferred embodiments, the inner panels 28 and outer panels 36 are substantially the same size so that they can be folded flat for storage. In an alternative form, the outer panels 36 can have a length less than the length of the inner panel 28 without interfering with the ability of the support member 14 to be folded flat during storage. In the embodiment illustrated in FIGS. 3, 4 and 5, the inner and outer panels 28, 36 are dimensioned to be only slightly longer than the base 12 when folded flat, thereby providing a compact folded head immobilizer device 10 and having a shorter length than the prior head immobilizer. In further embodiments, the panels 28 and 36 are dimensioned so that when folded flat extend only to the outer edges 74 of the base 12.

In use, the head immobilizer device 10 is placed under a patient's head in the collapsed condition of FIG. 4 with the patient's head resting on the center panel 18. The inner panels 28 are folded upwardly by pulling outwardly on slide tab 46 or on the lower end of outer panel 36, whereby the inner panel 28 conforms to the contour of the patient's head by the fold lines 42. The slide tabs 46 are slid outwardly toward the longitudinal ends of the base 12, whereby the outer panels 36 support the inner panels 28 in an upright position as shown in FIGS. 1 and 2. The distance the slide tabs 46 are slid outwardly depends on the size of the patient's head since the position of the slide tabs 46 determine the position and spacing of the inner panels 28 with respect to each other. A tab 82 is folded upwardly along the fold line 84 to engage the slide tab 46 and lock the slide tab 46 in position as shown in FIG. 1. A plurality of tabs 82 are formed in a longitudinal row as shown in FIG. 3 to adjust selectively the position of the head immobilizing support members 14. As shown, a tab 82 spaced toward the center of the head immobilizer 10 is selected for a small sized patient. Tabs 82 toward the edges 56 of the base 12 allow the tabs 46 to slide outward, thereby increasing the spacing between the inner panels 28.

The head immobilizer 10 can be secured to the spine board 16 by a double-sided adhesive tape 94 as shown in FIG. 5. The adhesive tape 94 includes a release liner 96 having an end 98 that extends through the cut portion 88 in the base. In this manner, the head immobilizer 10 can be placed on the spine board and the release liner 96 removed by pulling the end 96 through the cut portion to expose the adhesive tape 94, which then attaches the head immobilizer 10 to the spine board 16. The patient's head can be attached to the head immobilizer 10 by a suitable strap 89 or adhesive tape across the patient's forehead and/or chin to limit movement of the patient's head while transporting the patient as shown in FIG. 2. An adhesive tape can also be used to secure the position of the inner and outer panels with respect to the base and spine board. In further embodiments, the head immobilizer 10 is attached to the board 16 by hook and loop fasteners or other known attachment devices.

Referring to FIG. 9, a second embodiment of the invention is illustrated. In this embodiment, the head immobilizer 100 is similar in construction and operation to the embodiment of FIGS. 1–8. The head immobilizer 100 includes a head immobilizing support member 102 formed from a blank of a single sheet of material such as cardboard. The support member 102 includes a center panel 104 attached to a base 106 by a suitable fastener 108. Inner panels 110 are attached to the center panel 104 along a first edge 112 by a fold line 114. A second edge 116 of the inner panel 110 is coupled to an outer panel 118 by a fold line 120 at a first end of the panel 118. A second end of the outer panel 118 is coupled to a tab 126 along a fold line 128.

The base 106 has a substantially rectangular shape having a longitudinal dimension and a plurality of elongated slots 130 extending in the longitudinal direction. In the embodiment illustrated in FIG. 9, four elongated slots 130 are shown with two of the slots 130 being parallel and positioned adjacent the longitudinal ends 132 of the base 106. A fastener 134 extends through an aperture in the tab 126 and through a respective slot 130 to attach the tab 126 to the base 106 such that the tab can slide along the length of the slot 130. As shown in FIG. 11, the fasteners 134 have a head 136 at one end of a pin 138. A second head 140 is attached to the opposite end of the pin 138 to secure the fastener in the slots 130. The head 140 is slightly larger than the width of the slot 130 to retain the fastener in the slot while allowing sliding movement of the tab 126.

Base 106 further includes a plurality of apertures 142 extending in a line along the longitudinal dimension of the base 106. A pin or other fastener 144 is provided in the slide tabs 126 which can be pushed through to engage a selected aperture 142 to lock the tab in a selected position with respect to the base 106.

A third embodiment of the invention is illustrated in FIG. 10. FIG. 10 is a top plan view of the head immobilizer device 146. The head immobilizer 146 is similar to the head immobilizer 100 of FIG. 9 so that identical members are identified by the same reference number with the addition of a prime. The head immobilizer 146 includes a head support member 102' having a center panel 104' attached to a base 106'. An inner panel 110' and an outer panel 118' are connected together by a fold line 120'. In the embodiment of FIG. 10, the inner panel 110' and the outer panel 118' have a substantially trapezoidal shape and a triangular cut-out 148. Slide tabs 126' are attached to the outer panel 118' by a fold line 128'. Fasteners 134' extend through the tabs 126' to slide within slots 130' in the base 106'.

As shown in FIG. 10, the slide tabs 126' include a cut portion 150 to form a substantially triangular tab 152 connected to the slide tab 126' by a fold line 154. The base 106' includes a plurality of cut portions 156 defining substantially triangular shaped apertures 158. During use, the slide tab 126' is positioned above a selected aperture 158 and the triangular shaped tab 152 is pressed downwardly into the aperture 158 to lock the slide tab 126' into position with respect to the base 106'. In further embodiments, the base 106' can include a plurality of cut portions or tabs to cooperate with the tab 156 for locking the slide tab 126' in position.

While various embodiments have been chosen to illustrate the invention, it will be understood by those skilled in the art that various modifications and improvements can be made thereto without departing from the spirit and scope of the invention as defined in the appended claims.

What is claimed is:

1. A head immobilizer comprising:
  a base having a longitudinal dimension with longitudinal ends and a transverse dimension with transverse ends, said base further having a coupling member;
  a head immobilizing member attached to said base and including a pair of support members, each of said support members including an inner panel and an outer panel, said inner panel having a first edge hingedly connected to said base and a second edge, said inner panels forming a head immobilizing support structure, said outer panel having a first edge hinged to said second edge of said inner panel, said outer panels defining a support for supporting its respective inner panel in a fixed position with respect to said base;

a slide tab hingedly connected to a second edge of each said outer panel and being slidably coupled to said coupling member of said base for limited sliding movement in a longitudinal direction along said base, and a locking device for limiting sliding movement of each of said slide tabs with respect to said base.

2. The head immobilizer of claim 1, wherein each said slide tab is slidable toward said inner panel of its respective support member whereby said inner and outer panels are substantially parallel to each other and can be folded substantially flat against said base.

3. The head immobilizer of claim 1, wherein said base has first and second transverse edges and a slot extending along each of said transverse edges, and each of said slide tabs have an end received in a respective slot for sliding movement along a longitudinal dimension of said base.

4. The head immobilizer of claim 3, wherein said base includes a side panel coupled to each of said transverse edges along a fold line extending in a longitudinal direction with respect to said base, each of said side panels being folded inwardly and overlying said base to define said slots.

5. The head immobilizer of claim 4, wherein said side panels are attached to said base at longitudinal ends of said panels.

6. The head immobilizer of claim 5, wherein said side panels are stapled to said base at said longitudinal ends of said side panel.

7. The head immobilizer of claim 1, wherein said locking device comprises at least one locking tab on said base for engaging said slide tab connected to said outer panel and resisting sliding movement of said tab toward said longitudinal ends of said base.

8. The head immobilizer of claim 7, wherein said at least one locking tab is formed by a cut portion in said base, and said cut portion is connected to said base by a fold line, wherein said locking tab can be folded outward from a plane of said base to engage said slide tab.

9. The head immobilizer of claim 1, comprising a plurality of said locking devices spaced apart along said longitudinal dimension of said base for locking said slide tabs in a selected position with respect to said base.

10. The head immobilizer of claim 1, wherein said locking device is a pin extending through said slide tab and said base to fix the position of said slide tab with respect to said base.

11. The head immobilizer of claim 1, wherein said base includes at least one elongated slot extending in a longitudinal direction, and a pin extending through said slide tab and said slot for sliding movement therein, wherein said pin includes an enlarged head at opposite ends thereof to retain said pin in said slot.

12. The head immobilizer of claim 1, wherein said inner and outer panels have a substantially trapezoidal shape.

13. The head immobilizer of claim 1, wherein said locking device comprises a cut portion in said slide tab defining a locking tab hinged to said slide tab, and a plurality of apertures in said base, said apertures being aligned in a row extending in a longitudinal direction with respect to said base and being dimensioned for receiving said locking tab.

14. A head immobilizer comprising:

a base having a longitudinal dimension with opposite longitudinal edges, and a transverse dimension with opposite transverse side edges;

a side panel coupled to said base adjacent each said transverse side edge, each said side panels being substantially parallel to and overlying said base to define a pair of longitudinal slots along said transverse side edges of said base;

a pair of head support members attached to said base, each of said support members including an inner head immobilizing support panel and an outer support panel, said inner panel having a first edge hinged to said base and a second end opposite said first end, said outer panel having a first edge hinged to said second edge of said inner panel and a second edge opposite said first edge, said inner panels together being oriented to cradle a patient's head and said outer panels supporting said inner panels in a head cradling position;

each said outer panels having a slide tab having a first longitudinal edge hinged to said second edge of a respective outer panel, said slide tab having opposite transverse ends received in a respective longitudinal slot for sliding movement therein in a longitudinal direction with respect to said base, wherein said sliding movement of said slide tabs selectively adjusts the space between said inner panels.

15. The head immobilizer of claim 14, wherein said side panels have opposite longitudinal ends coupled to said base to define said longitudinal slots.

16. The head immobilizer of claim 14, wherein said side panels are coupled to said base by a longitudinal fold line.

17. The head immobilizer of claim 14, further comprising at least one locking device for locking said slide tab in a selected position with respect to said base.

18. The head immobilizer of claim 14, further comprising a support panel connecting said first edges of said inner panels together, wherein said support panel is coupled to said base.

19. The head immobilizer of claim 14, wherein said slide tabs are slidable toward a center of said base whereby said inner and outer panels are substantially parallel to each other and can be folded substantially flat against said base.

20. The head immobilizer of claim 14, further comprising a plurality of locking tabs in said base for limiting sliding movement of said slide tab with respect to said base.

21. The head immobilizer of claim 20, wherein said locking tabs are defined by a cut portion in said base, and said locking tabs being coupled to said base by a fold line.

22. The head immobilizer of claim 14, wherein said inner panel includes a plurality of fold lines for conforming to a patient's head.

* * * * *